(12) United States Patent
Yacoub

(10) Patent No.: US 6,427,272 B1
(45) Date of Patent: Aug. 6, 2002

(54) ANESTHESIA PILLOW

(76) Inventor: Yacoub E. Yacoub, 2816 Rivers Edge Rd., Louisville, KY (US) 40222

( * ) Notice: Subject to any disclaimer, the term of this patent is extended or adjusted under 35 U.S.C. 154(b) by 0 days.

(21) Appl. No.: 09/870,760

(22) Filed: May 31, 2001

(51) Int. Cl.[7] ................................................. A61G 7/07
(52) U.S. Cl. ................................. 5/638; 5/639; 5/637
(58) Field of Search ........................... 5/636, 637, 638, 5/639, 640

(56) References Cited

U.S. PATENT DOCUMENTS

| | | | |
|---|---|---|---|
| 2,688,142 A | 9/1954 | Jensen | 5/338 |
| 3,366,106 A | 1/1968 | Yao et al. | 128/76 |
| 3,694,831 A | * 10/1972 | Treace | 5/638 |
| D271,834 S | * 12/1983 | Huntsinger | 5/638 |
| 4,617,691 A | * 10/1986 | Monti et al. | 5/636 |
| 4,752,064 A | * 6/1988 | Voss | 5/638 |
| 5,018,231 A | * 5/1991 | Wang | 5/636 |
| D337,914 S | * 8/1993 | McDonald | 5/638 |
| 5,269,035 A | * 12/1993 | Hartunian | 5/637 |
| 5,612,501 A | * 3/1997 | Michelson | 5/637 |
| 5,613,501 A | 3/1997 | Michelson | 128/846 |

* cited by examiner

Primary Examiner—Michael F. Trettel
(74) Attorney, Agent, or Firm—Joseph N. Breaux

(57) ABSTRACT

An anesthesia pillow formed from resilient foam. The anesthesia pillow having multiple tube access channels, a neck support channel and a throat receiving channel all in connection with a hub opening adapted for supporting the back of a user's head in one configuration and supporting the user's face while allowing access to the user's mouth and nose in a second configuration.

3 Claims, 5 Drawing Sheets

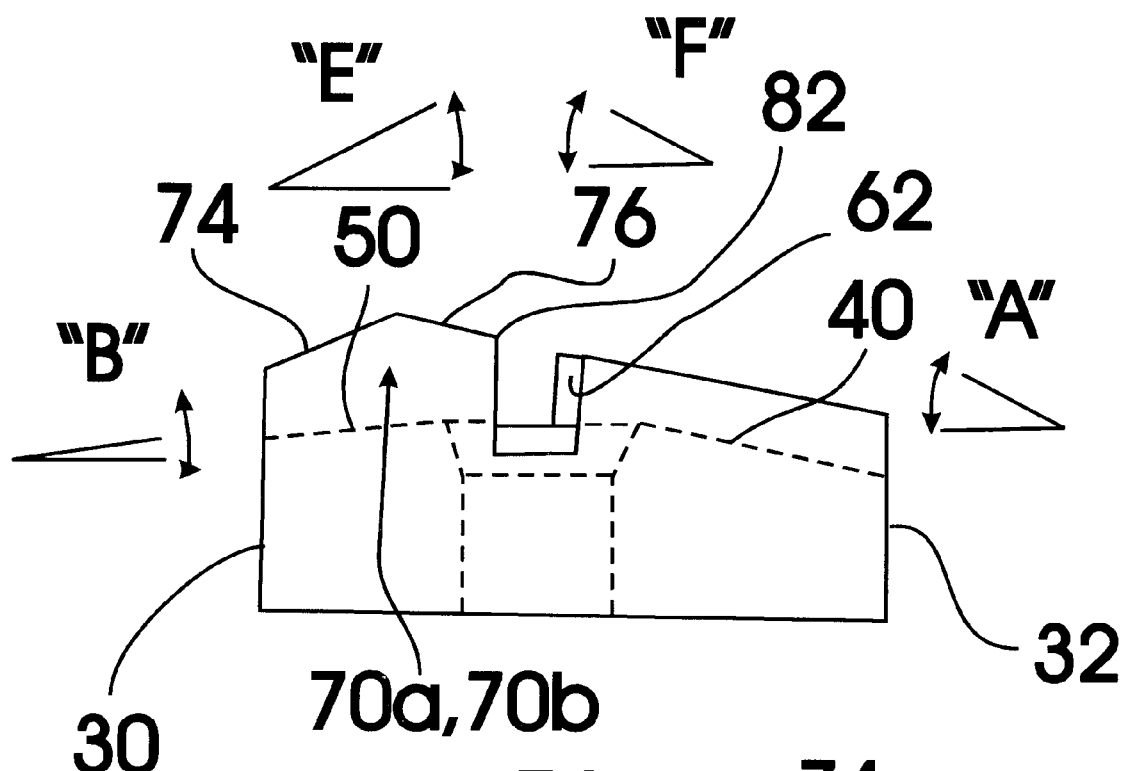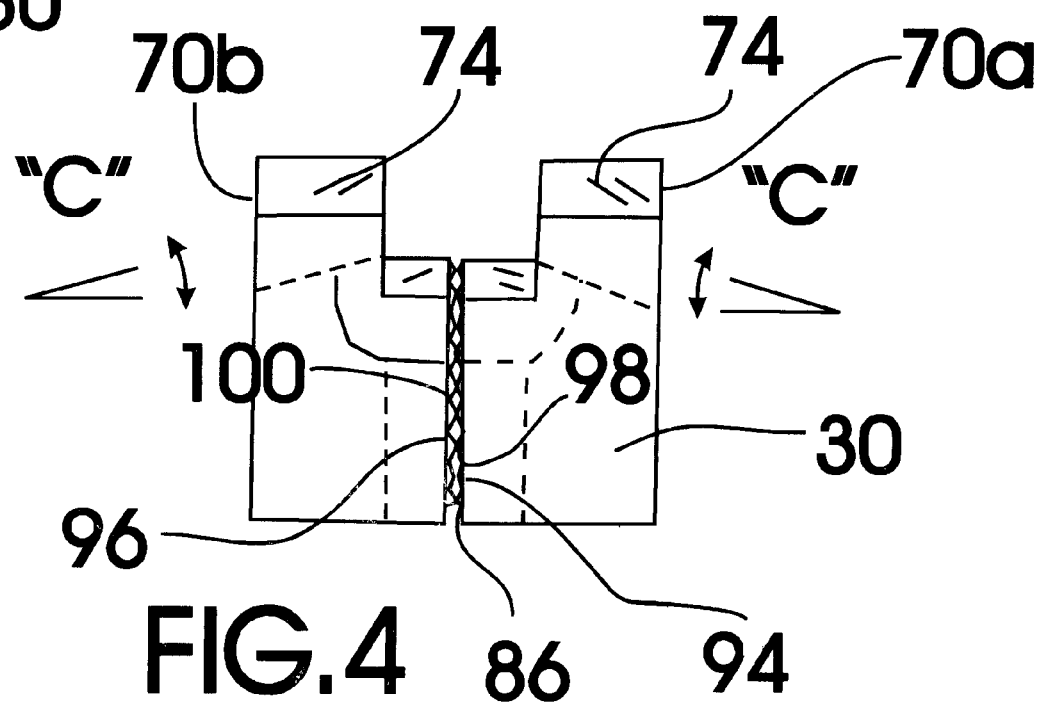

ANESTHESIA PILLOW

TECHNICAL FIELD

The present invention relates to pillows used to support the head of a patient during anesthesia and more particularly to an anesthesia pillow that includes a resilient foam pillow body having a substantially rectangular box shaped bottom portion having a bottom pillow surface with a rectangular-shaped perimeter, and a number of upper surfaces that define a neck support channel, two tube access channels and a throat receiving channel.

BACKGROUND ART

Many patients must be anesthetized before an operation. Because some operations require the patient to lie face down and others require the patient to lie face up, it would be desirable to have an anesthesia pillow that could be used for both types of operations. In addition, because it may be difficult or impossible for a patient to lift his/her head to have the pillow put in place, it would be desirable to have an anesthesia pillow that included a split to allow the pillow to be opened for positioning the pillow into place and closed once the pillow is properly in position.

GENERAL SUMMARY DISCUSSION OF INVENTION

It is thus an object of the invention to provide an anesthesia pillow that includes a resilient foam pillow body having a substantially rectangular box shaped bottom portion having a bottom pillow surface with a rectangular-shaped perimeter, and a number of upper surfaces that define a neck support channel, two tube access channels and a throat receiving channel.

Accordingly, an anesthesia pillow is provided. The anesthesia pillow includes a resilient foam pillow body having a substantially rectangular box shaped bottom portion having a bottom pillow surface with a rectangular-shaped perimeter, and a number of upper surfaces that define a neck support channel, two tube access channels and a throat receiving channel. The resilient foam pillow body further includes a hub opening formed through the bottom pillow surface into connection with the neck support channel, the two tube access channels and the throat receiving channel and a shoulder contact surface at one end oriented perpendicular to the bottom pillow surface and a collar bone contact surface opposite the shoulder contact surface and perpendicular to the bottom pillow surface. The throat receiving channel is open along a throat channel top thereof and has a first throat receiving channel end opening in connection with the hub opening, a second throat receiving channel end opening passing through the collar bone contact surface, and a throat receiving channel bottom surface oriented at an acute throat channel bottom angle of between ten and twenty degrees. The throat receiving channel bottom surface is farther from the bottom pillow surface at the first throat receiving channel end opening than at the second throat receiving channel end opening. The neck support channel is open along a neck support channel top thereof and has a first neck support channel end opening in connection with the hub opening, a second neck support channel end opening passing through the shoulder contact surface, and a neck support channel bottom surface oriented at an acute neck support angle of between ten and twenty degrees. The neck support channel bottom surface is farther from the pillow bottom surface at the first neck support channel end opening than at the second neck support channel end opening. Each of the tube access channels is a mirror image of the other. Each tube access channel is open along an access channel top thereof and has a first tube access channel end opening in connection with the hub opening, a second tube access channel end opening passing through the shoulder contact surface, and a tube access channel bottom surface oriented at an acute tube access channel angle of between ten and twenty degrees. Each tube access channel bottom surface is farther from the pillow bottom surface lower at the first tube access channel end opening than at the second tube access channel end opening. Each tube access channel has access channel sidewalls oriented at an angle of between ten and twenty degrees with respect to the shoulder contact surface such that the first tube access channel end opening is closer to the shoulder contact surface than the second tube access channel end opening. The neck support channel has a neck support structure along each side thereof between the first neck support channel end opening and the second neck support channel end opening. Each neck support structure has first and second, substantially, planar neck support structure top surfaces. The first neck support structure top surface is substantially rectangular and extends from the shoulder contact surface at a first neck support structure top surface angle of between fifteen and thirty degrees and terminates in a top surface contact edge. The second neck support structure top surface extends from an upper edge of an access channel sidewall at a second neck support structure top surface angle of between ten and twenty degrees and terminates in connection with a top surface contact edge. The first neck support structure top surface angle is greater than the second neck support structure top surface angle. The resilient foam pillow body has a split therethrough that passes entirely through the shoulder contact surface and continues through the resilient foam pillow body into connection with an entire hub opening defining surface closest to the shoulder contact surface in a manner to define a longitudinal hub opening access path between two, planar, facing, split-defining surfaces each of which is provided with hook and pile fastener material that is companionate with the hook and pile fastener material provided on the other planar, facing, split-defining surface.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 3 is a side plan view of the anesthesia pillow of FIG. 1.

FIG. 4 is a neck support end plan view of the anesthesia pillow FIG. 1.

EXEMPLARY MODE FOR CARRYING OUT THE INVENTION

Figure 1:
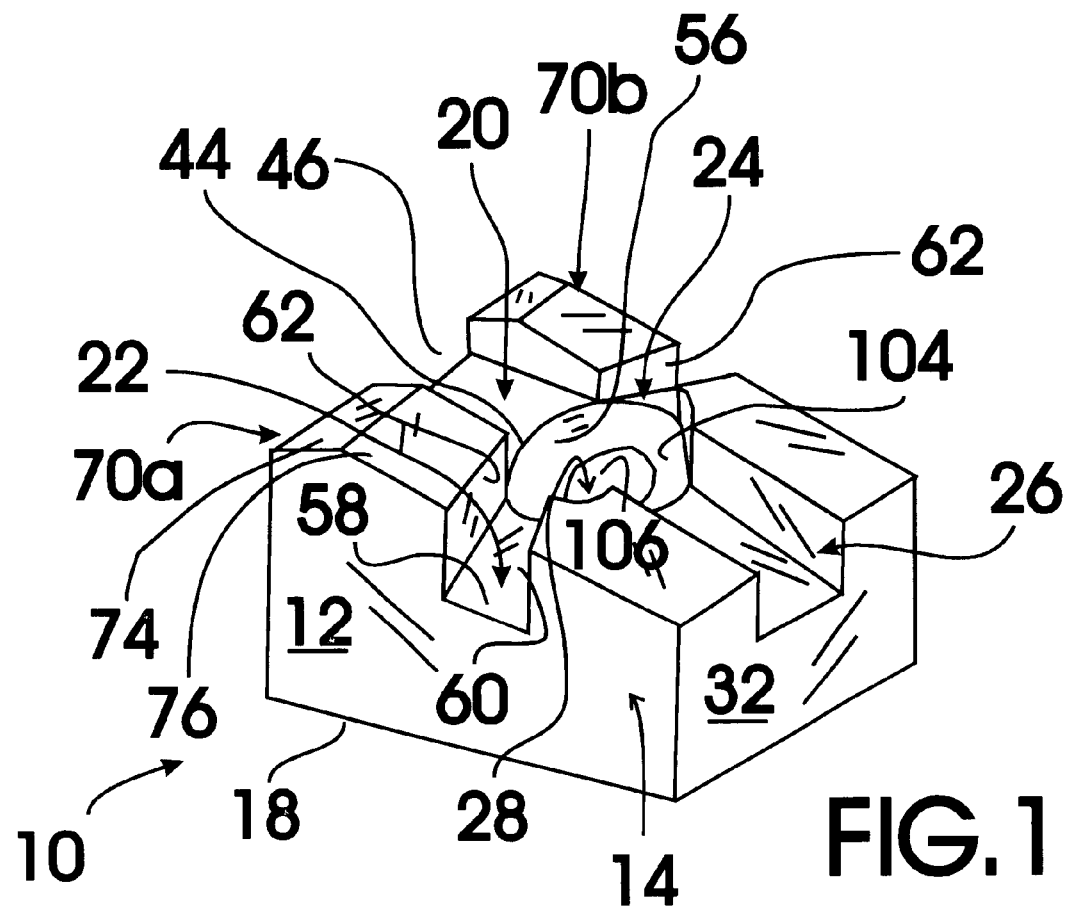
FIG. 1 is a perspective view of a first exemplary embodiment of the anesthesia pillow of the present invention.
Figure 2:
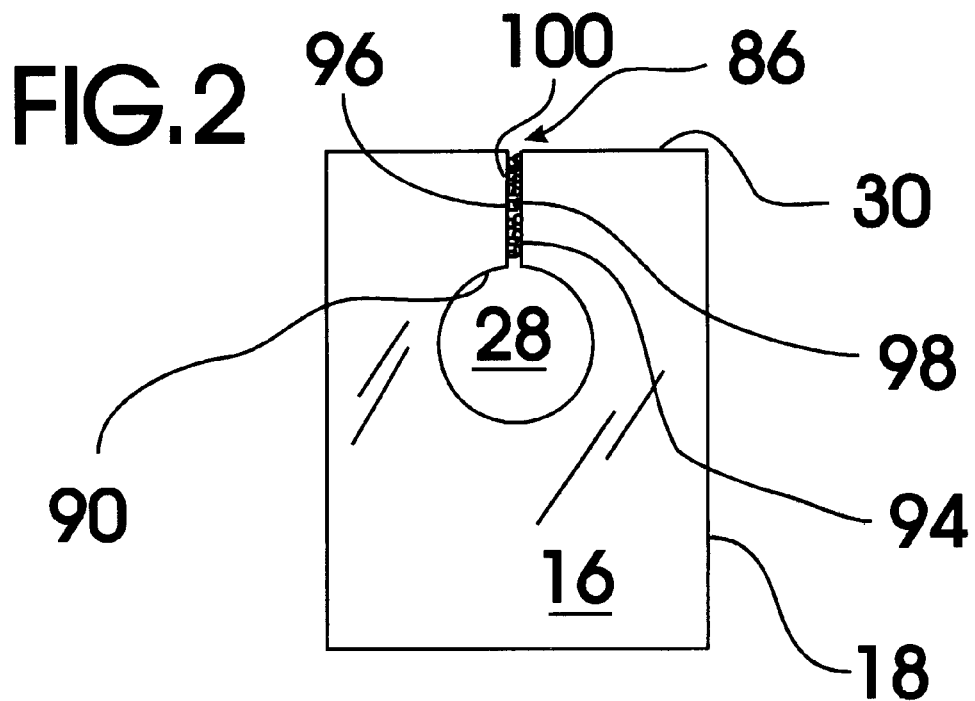
FIG. 2 is a bottom plan view of the anesthesia pillow of FIG. 1.
Figure 5:
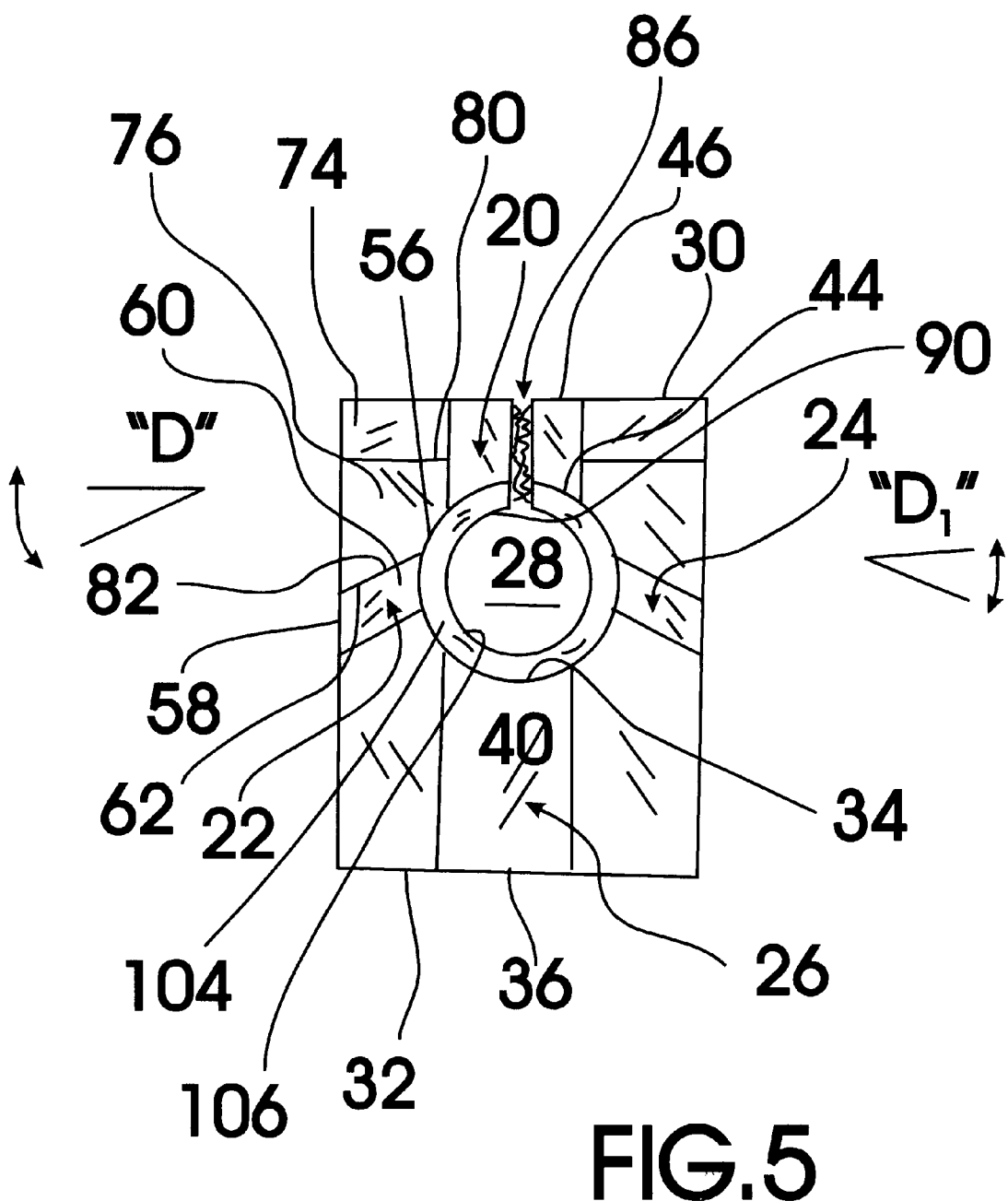
FIG. 5 is a top plan view of the anesthesia pillow FIG. 1.
Figure 6:
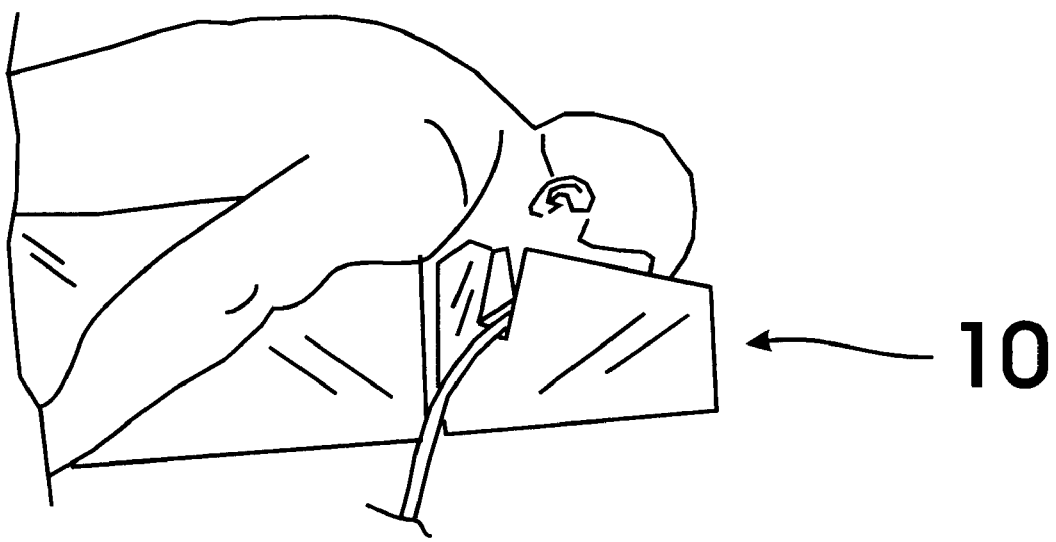
FIG. 6 is a side plan view of a representative user using the anesthesia pillow of FIG. 1 in the face down configuration.
Figure 7:
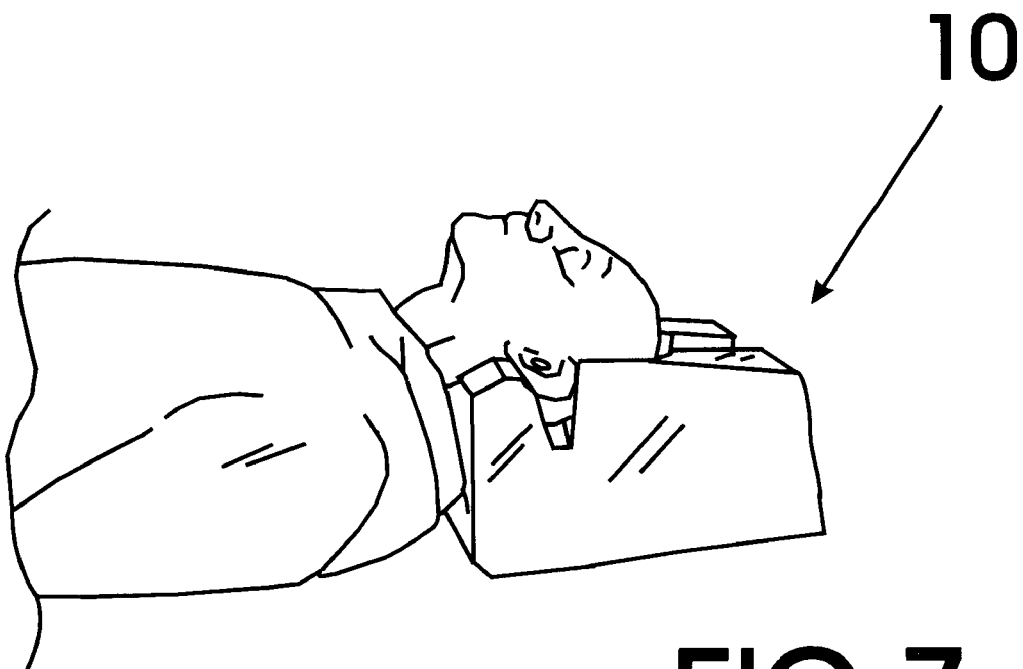
FIG. 7 is a side plan view of a representative user using the anesthesia pillow of FIG. 1 in the face up configuration.

FIGS. 1–7 show various aspects of a first exemplary embodiment of the anesthesia pillow of the present invention generally designated 10. Anesthesia pillow 10 includes a resilient foam pillow body, generally designated 12, having a substantially rectangular box shaped bottom portion, generally designated 14, having a bottom pillow surface 16 with a rectangular-shaped perimeter 18; and a number of upper surfaces that define a neck support channel, generally designated 20; two tube access channels, generally designated 22,24 respectively; and a throat receiving channel, generally designated 26. Resilient foam pillow body 12 also includes a hub opening 28 formed through bottom pillow surface 16 into connection with neck support channel 20, the two tube access channels 22,24 and throat receiving channel 26; a shoulder contact surface 30 at one end oriented perpendicular to the bottom pillow surface 16 and a collar bone contact surface 32 opposite the shoulder contact surface 30 and perpendicular to the bottom pillow surface 16.

Throat receiving channel 26 is open along a throat channel top thereof and has a first throat receiving channel end opening 34 in connection with hub opening 28, a second throat receiving channel end opening 36 passing through the collar bone contact surface 32, and a throat receiving channel bottom surface 40 oriented at an acute throat channel bottom angle "A" of fifteen degrees.

Neck support channel 20 is open along a neck support channel top thereof and has a first neck support channel end opening 44 in connection with hub opening 28, a second neck support channel end opening 46 passing through the shoulder contact surface 30, and a neck support channel bottom surface 50 oriented at an acute neck support angle "B" of twelve degrees.

Each tube access channel 22,24 is a mirror image of the other and is open along an access channel top thereof. Each tube access channel 22,24 has a first tube access channel end opening 56 in connection with hub opening, a second tube access channel end opening 58 passing through a respective one of two opposite resilient foam pillow body sides 17,19 each positioned between collar bone contact surface 32 and shoulder contact surface 30e, and a tube access channel bottom surface 60 oriented at an acute tube access channel angle "C"/"C" of fifteen degrees. Each tube access channel 22,24 having access channel sidewalls 62 that are oriented at a sidewall angle "D"/"$D_1$" of ten degrees with respect to shoulder contact surface 30 such that the first tube access channel end opening 56 is closer to shoulder contact surface 30.

Neck support channel 20 has a neck support structure 70a,70b along each side thereof between first neck support channel end opening 44 and second neck support channel end opening 46. Each neck support structure 70a,70b has first and second, substantially, planar neck support structure top surfaces 74,76. First neck support structure top surface 74 is substantially rectangular and extends from shoulder contact surface 30 at a first neck support structure top surface angle "E" of twenty-five degrees and terminates in a top surface contact edge 80. Second neck support structure top surface 76 extends from an upper edge 82 of an access channel sidewall at a second neck support structure top surface angle "F" of fifteen degrees and terminates in connection with top surface contact edge 80.

Resilient foam pillow body 14 has a split 86 therethrough that passes entirely through shoulder contact surface 30 and continues through the resilient foam pillow body 14 into connection with an entire hub opening defining surface 90 closest to shoulder contact surface 30 in a manner to define a longitudinal hub opening access path between two, planar, facing, split-defining surfaces 94,96 each of which is provided with hook and pile fastener material 98,100 that is companionate with the hook and pile fastener material provided on the other planar, facing, split-defining surface. In this embodiment hub opening 28 has a first semi-spherical surface 104 in connection with a circular tubular surface 106. In use, first semi-spherical surface 104 supports the back of the user's head when the patient is facing upward and the perimeter edge of the user's face while the user's nose and mouth are positioned in a tubular opening defined by circular tubular surface 106.

Figure 8:
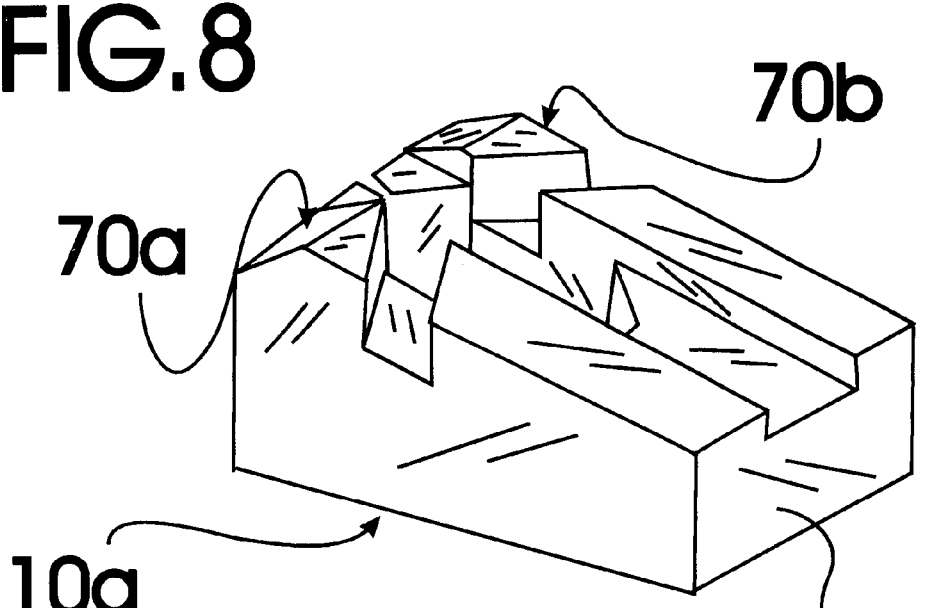
FIG. 8 is a perspective view of a second exemplary embodiment of the anesthesia pillow of the present invention.
Figure 9:
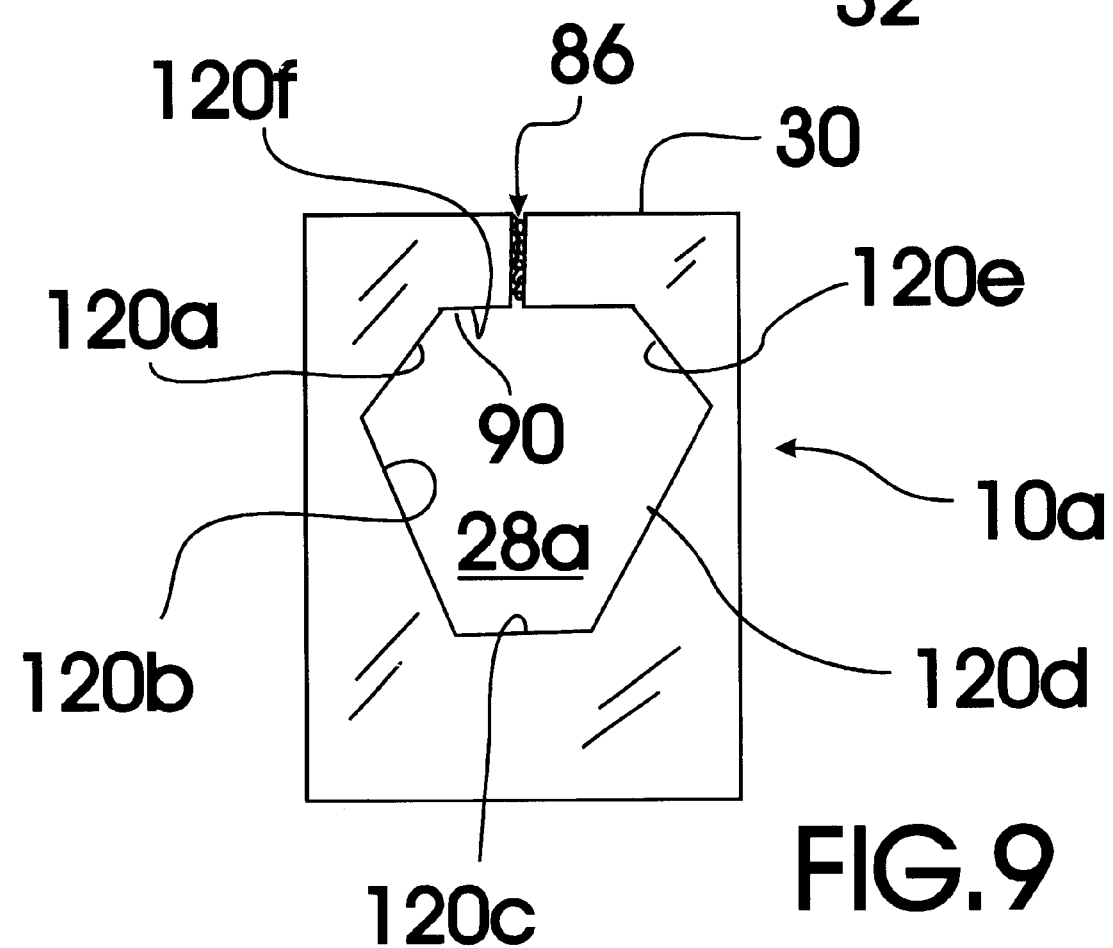
FIG. 9 is an underside plan view of the anesthesia pillow of FIG. 8.

FIGS. 8 and 9 show a second exemplary anesthesia pillow, generally designated 10a that is identical to anesthesia pillow 10 except that hub opening 28a is defined by six planar sidewalls 120a–f in a flat bottomed diamond shape along the entire length thereof.

It can be seen from the preceding description that an anesthesia pillow has been provided.

It is noted that the embodiment of the anesthesia pillow described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. An anesthesia pillow comprising:
   a resilient foam pillow body having a substantially rectangular box shaped bottom portion having a bottom pillow surface with a rectangular-shaped perimeter, and a number of upper surfaces that define a neck support channel, two tube access channels and a throat receiving channel;
   the resilient foam pillow body further including a hub opening formed through the bottom pillow surface into connection with the neck support channel, the two tube access channels and the throat receiving channel, a shoulder contact surface at one end oriented perpendicular to the bottom pillow surface, a collar bone contact surface opposite the shoulder contact surface and perpendicular to the bottom pillow surface, and two opposite resilient foam pillow body sides positioned between collar bone contact surface and shoulder contact surface;
   the throat receiving channel being open along channel top thereof and having a first throat receiving channel end opening in connection with the hub opening, a second throat receiving channel end opening passing through the collar bone contact surface, and a throat receiving channel bottom surface oriented at an acute throat channel bottom angle of between ten and twenty degrees;
   the throat receiving channel bottom surface being farther from the bottom pillow surface at the first throat receiving channel end opening than at the second throat receiving channel end opening;
   the neck support channel being open along a neck support channel top thereof and having a first neck support channel end opening in connection with the hub opening, a second neck support channel end opening passing through the shoulder contact surface, and a neck support channel bottom surface oriented at an acute neck support angle of between ten and twenty degrees;

the neck support channel bottom surface being farther from the pillow bottom surface at the first neck support channel end opening than at the second neck support channel end opening;

each of the tube access channels being a mirror image of the other;

each tube access channel being open along an access channel top thereof and having a first tube access channel end opening in connection with the hub opening, a second tube access channel end opening passing through a respective one of the opposite resilient foam pillow body sides, and a tube access channel bottom surface oriented at an acute tube access channel angle of between ten and twenty degrees;

each tube access channel bottom surface being farther from the pillow bottom surface lower at the first tube access channel end opening than at the second tube access channel end opening;

each tube access channel having access channel sidewalls oriented at an angle of between ten and twenty degrees with respect to the shoulder contact surface such that the first tube access channel end opening is closer to the shoulder contact surface than the second tube access channel end opening;

the neck support channel having a neck support structure along each side thereof between the first neck support channel end opening and the second neck support channel end opening;

each neck support structure having first and second, substantially, planar neck support structure top surfaces;

the first neck support structure top surface being substantially rectangular and extending from the shoulder contact surface at a first neck support structure top surface angle of between fifteen and thirty degrees and terminating in a top surface contact edge;

the second neck support structure top surface extending from an upper edge of an access channel sidewall at a second neck support structure top surface angle of between ten and twenty degrees and terminating in connection with a top surface contact edge;

the first neck support structure top surface angle being greater than the second neck support structure top surface angle;

the resilient foam pillow body having a split therethrough that passes entirely through the shoulder contact surface and continues through the resilient foam pillow body into connection with an entire hub opening defining surface closest to the shoulder contact surface in a manner to define a longitudinal hub opening access path between two, planar, facing, split-defining surfaces each of which is provided with hook and pile fastener material that is companionate with the hook and pile fastener material provided on the other planar, facing, split-defining surface.

2. The anesthesia pillow of claim 1 wherein:

the hub opening is defined by multiple planar side surfaces.

3. The anesthesia pillow of claim 1 wherein:

the hub opening is defined by a first semi-spherical surface in connection with a circular tubular surface;

a spherical radius of the semi-spherical surface being greater than a circular radius of the circular tubular surface.

* * * * *